United States Patent
Purcell

(10) Patent No.: US 7,485,145 B2
(45) Date of Patent: Feb. 3, 2009

(54) ARTIFICIAL INTERVERTEBRAL DISC ASSEMBLY

(75) Inventor: Thomas Purcell, Del Mar, CA (US)

(73) Assignee: Alphatec Spine, Incorporated, Carlsbad, CA (US)

( * ) Notice: Subject to any disclaimer, the term of this patent is extended or adjusted under 35 U.S.C. 154(b) by 207 days.

(21) Appl. No.: 11/062,782

(22) Filed: Feb. 22, 2005

(65) Prior Publication Data

US 2005/0273169 A1    Dec. 8, 2005

Related U.S. Application Data

(60) Provisional application No. 60/547,035, filed on Feb. 23, 2004.

(51) Int. Cl.
A61F 2/44        (2006.01)
(52) U.S. Cl. .................................. 623/17.12; 623/17.11
(58) Field of Classification Search .... 623/17.11–17.16
See application file for complete search history.

(56) References Cited

U.S. PATENT DOCUMENTS

| | | | | |
|---|---|---|---|---|
| 4,349,921 A * | 9/1982 | Kuntz | .................. | 623/17.16 |
| 4,759,769 A * | 7/1988 | Hedman et al. | .......... | 623/17.13 |
| 4,863,477 A * | 9/1989 | Monson | .................. | 623/17.12 |
| 4,932,969 A * | 6/1990 | Frey et al. | ................ | 623/17.12 |
| 4,932,975 A * | 6/1990 | Main et al. | ............... | 623/17.12 |
| 5,108,438 A * | 4/1992 | Stone | ..................... | 623/17.16 |
| 5,480,442 A * | 1/1996 | Bertagnoli | ............... | 623/17.14 |
| 6,096,080 A * | 8/2000 | Nicholson et al. | ........ | 623/17.16 |
| 6,395,032 B1 | 5/2002 | Gauchet | ................... | 623/17.12 |
| 6,613,091 B1 * | 9/2003 | Zdeblick et al. | .......... | 623/17.16 |
| 6,692,495 B1 * | 2/2004 | Zacouto | ..................... | 606/61 |
| 6,875,235 B2 * | 4/2005 | Ferree | ..................... | 623/20.32 |
| 6,981,989 B1 * | 1/2006 | Fleischmann et al. | .... | 623/17.11 |
| 7,066,957 B2 * | 6/2006 | Graf | ......................... | 623/17.12 |

(Continued)

FOREIGN PATENT DOCUMENTS

FR        2 723 841 A        3/1996

(Continued)

OTHER PUBLICATIONS

International Search Report dated Jun. 23, 2006 corresponding to PCT/US2006/006166.

*Primary Examiner*—William H. Matthews
*Assistant Examiner*—Ann Schillinger
(74) *Attorney, Agent, or Firm*—Mintz, Levin, Cohn, Ferris, Glovsky and Popeo PC

(57) ABSTRACT

An artificial intervertebral disc assembly including upper and lower end plates, an expandable bladder carried by the end plates and circumscribing a containment area therebetween. A biocompatible fluid is disposed within the containment area. A cylinder having a plurality of apertures therein projects from the lower plate into the containment area. A piston having a curvilinear upper surface is reciprocally moveable within the cylinder and projects from the open end thereof. A cylindrical projection depending from the upper plate bears against and mates with the upper surface of the piston so as to allow relative rotational movement of the end plates into and out of parallel alignment. By varying the size of the apertures in the cylinder and the elasticity of the bladder, the amount of axial load necessary to effect inward movement of the end plates can be varied.

15 Claims, 3 Drawing Sheets

U.S. PATENT DOCUMENTS

| | | | |
|---|---|---|---|
| 2002/0151978 A1* | 10/2002 | Zacouto et al. | 623/17.12 |
| 2003/0009226 A1* | 1/2003 | Graf | 623/17.16 |
| 2003/0045939 A1 | 3/2003 | Casutt | 623/17.15 |
| 2004/0019356 A1* | 1/2004 | Fraser et al. | 606/102 |
| 2005/0055094 A1* | 3/2005 | Kuslich | 623/17.11 |
| 2005/0060036 A1* | 3/2005 | Schultz et al. | 623/17.15 |
| 2005/0192674 A1* | 9/2005 | Ferree | 623/23.41 |
| 2005/0216084 A1* | 9/2005 | Fleischmann et al. | 623/17.11 |
| 2006/0235535 A1* | 10/2006 | Ferree et al. | 623/17.16 |

FOREIGN PATENT DOCUMENTS

| | | |
|---|---|---|
| WO | WO 02/30337 A | 4/2002 |

* cited by examiner

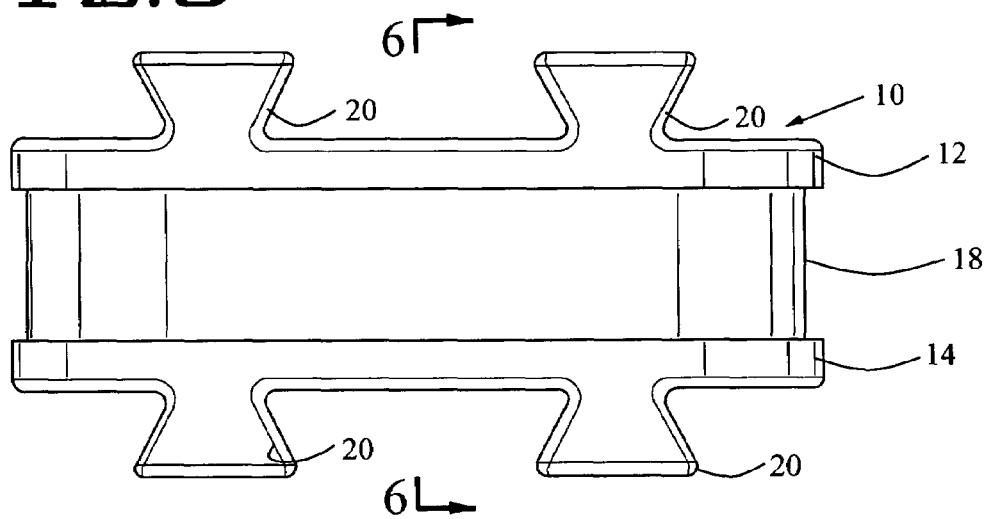
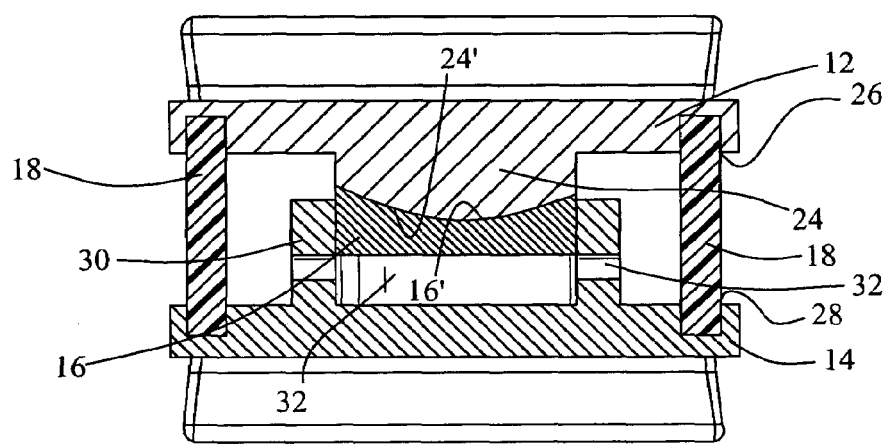

ARTIFICIAL INTERVERTEBRAL DISC ASSEMBLY

CROSS-REFERENCE TO RELATED APPLICATIONS

This application claims the benefit of U.S. Provisional Patent Application Ser. No. 60/547,035, filed Feb. 23, 2004.

BACKGROUND OF THE INVENTION

The present invention relates to an artificial intervertebral disc assembly which is implanted in the vacated space after a diseased or damaged intervertebral disc has been removed. It is important that such assemblies remain parallel to and fixed against the end plates of the vertebral body when subjected to off-axis loading so as to mimic the loading characteristics of a natural disc and provide the patient with substantially the same range of motion as would be provided by a healthy natural disc. It is also important for the comfort of the patient if the stiffness of the disc assembly can be set depending on the size of the patient. The assembly of the present invention obtains these objectives.

SUMMARY OF THE INVENTION

The disc assembly of the present invention is generally oval-shaped, provided in different sizes to cover the end plates of the vertebral bodies of differently sized patients and employs a novel bladder and piston dampening assembly that axially biases the end plates of the disc assembly outwardly against the end plates of the vertebral body, allows for variations in the stiffness of the assembly for differently sized patients as well as pivotal movement and shock absorption under a wide range of physiological loading conditions while continually maintaining each of the assembly end plates in a parallel abutting relationship with the adjacent end plate of the vertebral body. The end plates of the disc assembly are each provided with outwardly projecting fixation features to decrease the chance of the implanted disc assembly migrating after implantation. The result of these features is a substantial improvement in artificial intervertebral disc replacement devices.

BRIEF DESCRIPTION OF THE DRAWINGS

FIG. 5 is a side view of the artificial intervertebral disc assembly of the present invention.

FIG. 6 is a sectional view of the intervertebral disc assembly of the present invention taken along the line 6-6 in FIG. 5.

DETAILED DESCRIPTION OF THE PREFERRED EMBODIMENT

Figure 1:
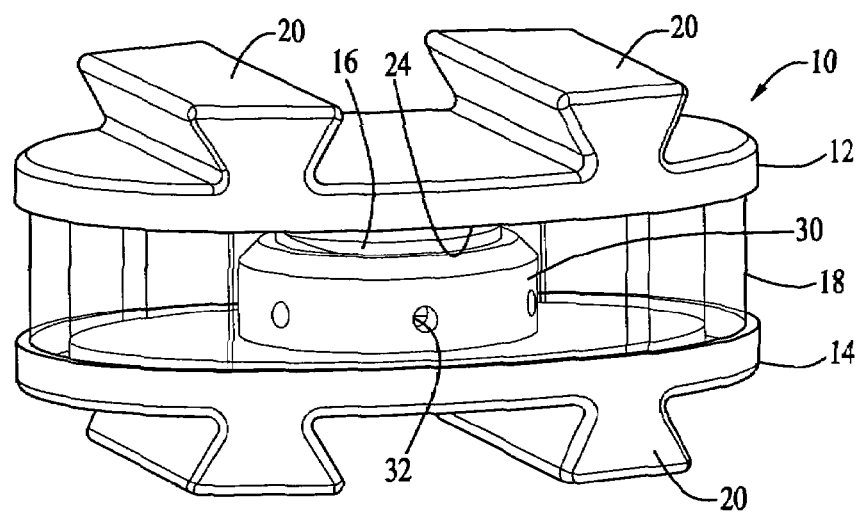
FIG. 1 is a perspective view of the artificial intervertebral disc assembly of the present invention.

Referring now in detail to the drawings, the artificial intervertebral disc assembly 10 of the present invention comprises a pair of end plates 12 and 14, a piston 16 and a bladder 18. End plates 12 and 14 are preferably of an oval configuration with medial-lateral and anterior-poster dimensions in the same ratio as natural vertebral bodies and are preferably constructed of a titanium alloy, Cobalt-Chromium-Molybdenum alloys and the like or a radiolucent material such as polyetherketoneketone or polyetheretherketone (PEKK/PEEK), although they could be formed of other biologically acceptable inert materials that would provide the plates 12 and 14 with a rigid structure.

The end plates 12 and 14 each define some form of fixation feature on their outer surfaces for engaging the end plates of the vertebral body (not shown) so as to decrease the chance the implant migration after implantation and to promote bone in-growth. In the embodiment of the invention illustrated in the drawings, two or more dove-tailed projections 20 are employed. Such dove-tailed projections engage mating surfaces formed by the surgeon in the end plates of the vertebral body. Alternatively, a plurality of outwardly projecting spikes, ribs or ridges or other convex surfaces that mate with the natural vertebral end plates could be employed to secure the end plates of assembly 10 in place against the natural vertebral end plates. Long-term stabilization of the implant may occur using a porous coating such as beads, an hydroxyappetite coating or plasma spray to promote bone in-growth.

Figure 3:
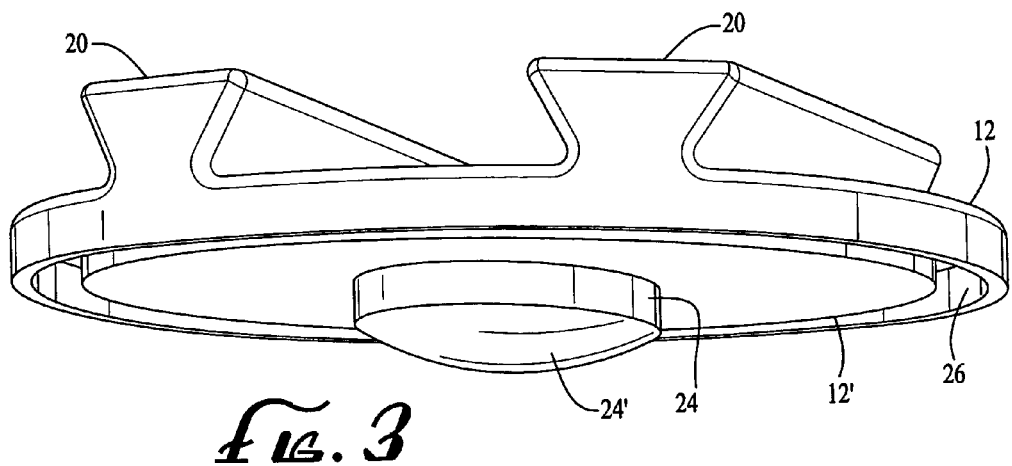
FIG. 3 is a perspective view of the upper end plate of the disc assembly of the present invention.
Figure 4:
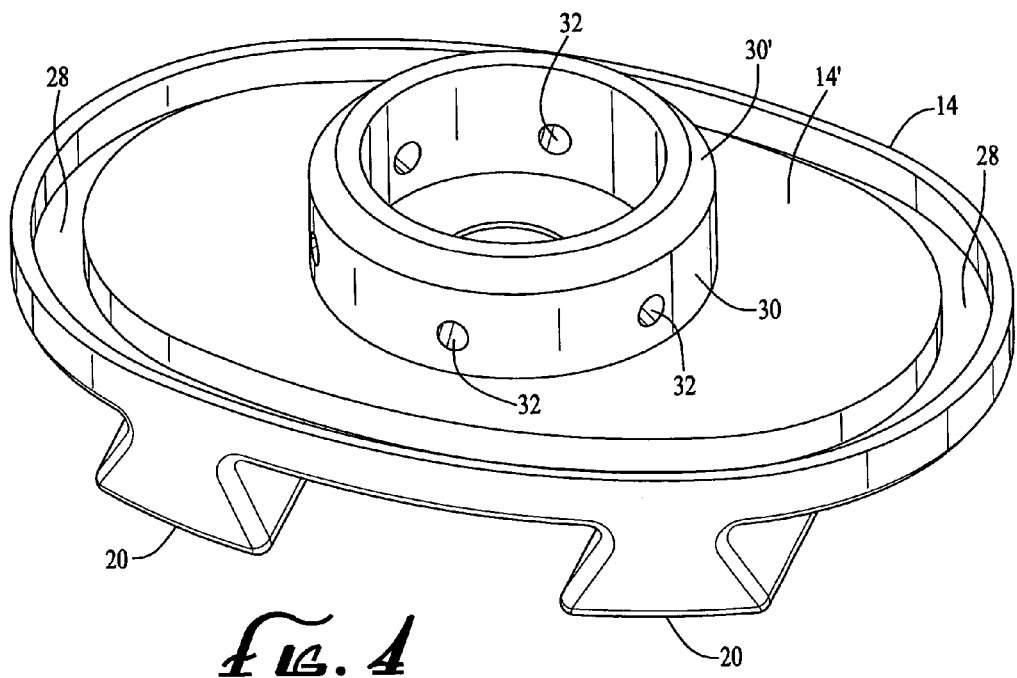
FIG. 4 is a perspective view of the lower end plate of the disc assembly of the present invention.

The inwardly facing surface 12' of the first or upper end plate 12, as shown in the drawings, defines a cylindrical projection 24 terminating in a convex end face 24' and a groove 26 extending about the perimeter of inner surface 12' (see FIG. 3). The inner surface 14' of the second or lower end plate 14 defines a corresponding opposed groove 28 extending about the perimeter thereof and a cylinder 30 projecting upwardly from the central portion of surface 14'. Cylinder 30 defines a plurality of radially extending channels 32 extending therethrough and is sized to receive reciprocating piston 16 therein. The upper end surface of cylinder 30 is preferably beveled at 30' as illustrated in FIG. 4. The upper surface 16' of piston 16 is of a concave configuration so as to mate with the convex lower end face 24' on the depending projection 24 on the first end plate 12 (see FIG. 6). The piston 16 is reciprocally moveable within cylinder 30 and is provided with a height or axial length sufficient to project from cylinder 30 as shown in the drawings and as will be further discussed.

Figure 2:
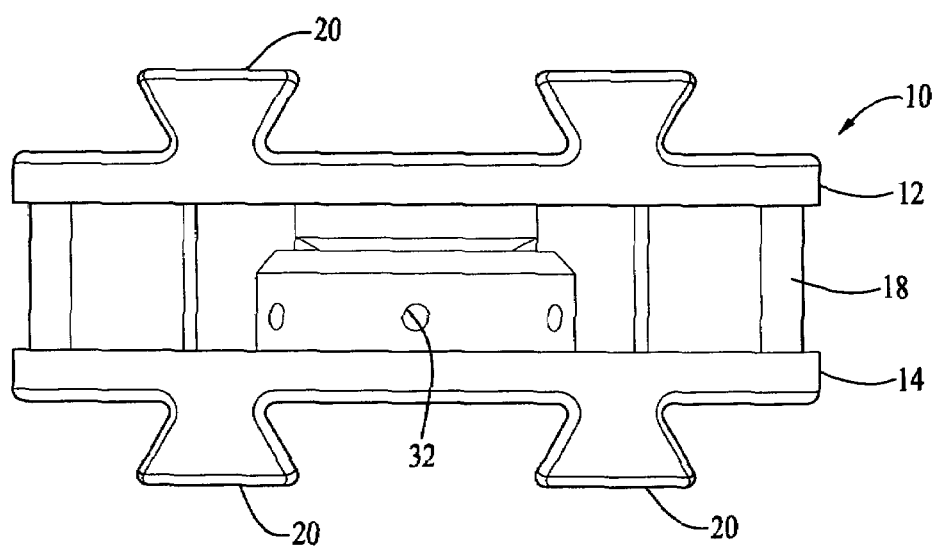
FIG. 2 is a side view of the artificial intervertebral disc assembly of the present invention with the inflatable bladder being shown as transparent so as to show the positioning thereof and not to obscure the interior of the disc assembly.

Bladder 18 extends between end plates 12 and 14 and is held at its upper and lower end portions in perimeter grooves 26 and 28 so as to circumscribe and enclose the space between the end plates 12 and 14 disposed about piston 16 and cylinder 30 as shown in FIGS. 1 and 2. Bladder 18 is preferably formed of a flexible polymer material and is secured in place by a suitable epoxy adhesive or, alternatively, by a mechanical connection such as a pair of locking rings (not shown) carried by the two end plates 12 and 14 or another suitable mechanical attachment device.

The space disposed interiorly of the end plates 12 and 14 and bladder 18, including the interior of cylinder 30 is filled with a biocompatible fluid 31 such as saline or hydrogel. Piston 16 actually floats in the fluid 31 within cylinder 30. Accordingly, when an axially directed compressive force is exerted on the end plates 12 or 14 or both, the piston 16 is forced downwardly in the cylinder, causing fluid 31 in the area between the piston and the bottom of the cylinder 30 to pass outwardly through the radial channels 32 in the cylinder wall, bulging the bladder 18 outwardly. Upon a relaxation of the axial pressure against the end plates, the resiliency in the bladder will cause fluid to move inwardly through channels 32, returning the assembly 10 to its pre-stressed configuration.

By sizing the channels 32, and varying the elasticity of bladder 18, the stiffness of the disc assembly, i.e., the axial force necessary to effect the outward bulging or deformation of the bladder and thus relative movement of the end plates can be regulated to accommodate individuals of varying size and enable the disc assembly 10 to mimic the physiological characteristics of a natural healthy intervertebral disc and provide such individuals with a relatively full range of motion.

As seen in the drawings, the mating curvatures of the axially aligned upper surface 16' of piston 16 and convex end face 24' on projection 24 and the positioning of the interface of those surfaces outside the confines of the cylinder 30 allows relative rotational movement of the end plates about a plurality of axes while maintaining the abutment of projection 24 against piston 16. By providing rotation about a plurality of axes, the two end plates 12 and 14 are allowed to move into non-parallel orientations whereby the assembly 10 accommodates off-axial loading and mimics the distortion of a natural disc without adversely affecting the support function between the two end plates 12 and 14 that is provided by the piston 16 and cylinder 30.

Various changes and modifications may be made in carrying out the present invention without departing from the spirit and scope thereof. Insofar as these changes and modifications are within the purview of the appended claims, they are to be considered as part of the present invention.

What is claimed is:

1. An artificial intervertebral disc assembly adapted to be implanted adjacent end plates of vertebral bodies following the removal of a diseased or damaged intervertebral disc, said assembly comprising: an upper end plate; a lower end plate, said upper and lower end plates each defining an inner surface and an outer vertebral body engaging surface; an expandable bladder carried by said upper and lower end plates and circumscribing a fluid containment area therebetween; a biocompatible fluid disposed within said containment area between said upper and lower end plates; a cylinder projecting from said inner surface of said lower end plate into said containment area and having an open upper end; a piston reciprocally moveable within said cylinder and projecting from said open end thereof, said piston defining a curvilinear upper surface; a projection depending from said inner surface of said upper end plate into said containment area, said projection defining a curvilinear lower surface for mating with said upper surface of said piston so as to allow relative rotational movement of said upper and lower end plates and into and out of parallel alignment and a plurality of fluid flow apertures disposed in said cylinder below said piston.

2. The assembly of claim 1 wherein said upper and lower end plates are oval-shaped.

3. The assembly of claim 1 wherein said outer surfaces on said upper and lower end plates define a plurality of spikes, ribs or ridges thereon for engaging the end plates of the vertebral bodies and preventing migration of said assembly.

4. The assembly of claim 3 wherein said upper and lower end plates are oval-shaped.

5. The assembly of claim 1 wherein said outer surfaces of said upper and lower end plates define dove-tailed projections thereon for engaging mating surfaces formed in the end plates of the vertebral bodies and preventing migration of said assembly.

6. The assembly of claim 5 wherein said upper and lower end plates are oval-shaped.

7. The assembly of claim 1 wherein said expandable bladder is formed of a flexible polymer material having a predetermined measure of elasticity and wherein said apertures in said cylinder collectively define a fluid flow area of predetermined size, said area cooperating with said measure of elasticity to define the desired axial force necessary to effect relative inward movement of said upper and lower end plates.

8. The assembly of claim 7 wherein said upper and lower end plates are oval-shaped.

9. The assembly of claim 7 wherein said outer surfaces on said upper and lower end plates define a plurality of spikes, ribs or ridges thereon for engaging the end plates of the vertebral bodies and preventing migration of said assembly.

10. The assembly of claim 7 wherein said outer surfaces of said upper and lower end plates define dove-tailed projections thereon for engaging mating surfaces formed in the end plates of the vertebral bodies and preventing migration of said assembly.

11. An artificial intervertebral disc assembly adapted to be implanted adjacent end plates of vertebral bodies following the removal of a diseased or damaged intervertebral disc, said assembly comprising: an upper end plate; a lower end plate, said upper and lower end plates each defining an inner surface and an outer vertebral body engaging surface; an expandable bladder having a predetermined measure of elasticity carried by said upper and lower end plates and circumscribing a fluid containment area therebetween; a biocompatible fluid disposed within said containment area between said upper and lower end plates; a cylinder projecting from said inner surface of said lower end plate into said containment area and having an open upper end; a piston reciprocally moveable within said cylinder and projecting from said open end thereof, said piston defining a curvilinear upper surface; a projection depending from said inner surface of said upper end plate into said containment area, said projection defining a curvilinear lower surface for mating with said upper surface of said piston so as to allow relative rotational movement of said upper and lower end plates and into and out of parallel alignment and a plurality of fluid flow apertures of predetermined size disposed in said cylinder below said piston whereby inward movement of said upper and lower end plates will cause fluid in said cylinder to pass outwardly through said apertures therein and expand said bladder such that variations in the collective area defined by said apertures and the elasticity of said bladder will vary the amount of axial load necessary to effect such inward movement of said upper and lower end plates.

12. The assembly of claim 11 wherein said upper and lower end plates are oval-shaped.

13. The assembly of claim 11 wherein said outer surfaces on said upper and lower end plates define a plurality of spikes, ribs or ridges thereon for engaging the end plates of the vertebral bodies and preventing migration of said assembly.

14. The assembly of claim 11 wherein said outer surfaces of said upper and lower end plates define dove-tailed projections thereon for engaging mating surfaces formed in the end plates of the vertebral bodies and preventing migration of said assembly.

15. The assembly of claim 11 wherein the expandable bladder comprises a polymer.

* * * * *